US00PP31739P2

(12) United States Plant Patent
Yokota

(10) Patent No.: US PP31,739 P2
(45) Date of Patent: May 12, 2020

(54) ***ROSA* PLANT NAMED 'ROP007'**

(50) Latin Name: ***Rosa* hybrid**
Varietal Denomination: ROP007

(71) Applicant: Tomoki Yokota, Aichi (JP)

(72) Inventor: Tomoki Yokota, Aichi (JP)

( * ) Notice: Subject to any disclaimer, the term of this patent is extended or adjusted under 35 U.S.C. 154(b) by 0 days.

(21) Appl. No.: 16/501,986

(22) Filed: Jul. 16, 2019

(51) Int. Cl.
*A01H 5/02* (2018.01)
*A01H 6/74* (2018.01)

(52) U.S. Cl.
USPC ..... Plt./101
CPC ..... *A01H 6/74* (2018.05)

(58) Field of Classification Search
USPC ..... Plt./101, 116, 123
CPC ..... A01H 5/0222
See application file for complete search history.

*Primary Examiner* — Kent L Bell
(74) *Attorney, Agent, or Firm* — Penny J. Aguirre

(57) ABSTRACT

A new cultivar of *Rosa* plant named 'ROP007' that is characterized by its thornless stems, its dwarf plant habit, its floriferous and abundant blooming habit producing small pink flowers with white centers, and its lack of fruit production.

2 Drawing Sheets

Botanical classification: *Rosa* hybrid.
Variety denomination: 'ROP007'.

BACKGROUND OF THE INVENTION

The present invention relates to a new and distinct cultivar of *Rosa* of hybrid origin. The new cultivar will be referred to hereafter by its cultivar name, 'ROP007'. 'ROP007' is a new cultivar of hybrid rose grown for use as a container and landscape plant.

The new cultivar was derived from a breeding program by the Inventor in Inazawa-shi, Aichi, Japan. The goal of the breeding was to produce a new cultivar of rose with a dwarf plant habit, prolific flowering and thornless stems. The Inventor made a cross in 1984 between an unnamed proprietary plant in the Inventor's breeding program as both the female and male parents. The exact characteristics of the parents are unknown as seeds where pooled and sown from several crosses. The Inventor selected 'ROP007' in summer of 2008 as a single unique plant amongst the seedlings that resulted from the above crosses.

Asexual propagation of the new cultivar was first accomplished by stem cuttings by the Inventor in 2009 in Inazawa-shi, Aichi, Japan. Asexual propagation by stem cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'ROP007' as a unique cultivar of *Rosa*.

1. 'ROP007' exhibits thornless stems.
2. 'ROP007' exhibits a dwarf plant habit.
3. 'ROP007' exhibits a floriferous and abundant blooming habit producing small pink flowers with white centers.
4. 'ROP007' exhibits no fruit production.

'ROP007' can be compared to the *Rosa* cultivars 'Azumino' (not patented), 'Nozomi' (not patented) and 'Yomeotome' (not patented). 'Azumino' is similar to 'ROP007' in having flowers that are pink in color with white centers and in having an abundant blooming habit. 'Azumino' differs from 'ROP007' in producing fruit and in having stems with thorns, a less dwarf plant habit and flowers that are larger in size. 'Nozomi' differs from 'ROP007' in having larger flowers, a much taller plant habit, and in having stems with thorns. 'Yomeotome' differs from 'ROP007' in having longer stems and a more creeping plant habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics of the new *Rosa*. The photographs were taken of a three-year-old plant of 'ROP007' as grown in a greenhouse in a 3-liter container with a single prune in spring in Boskoop, The Netherlands.

The photograph in FIG. 1 provides a side view of a plant of 'ROP007' in bloom.

Figure 1:
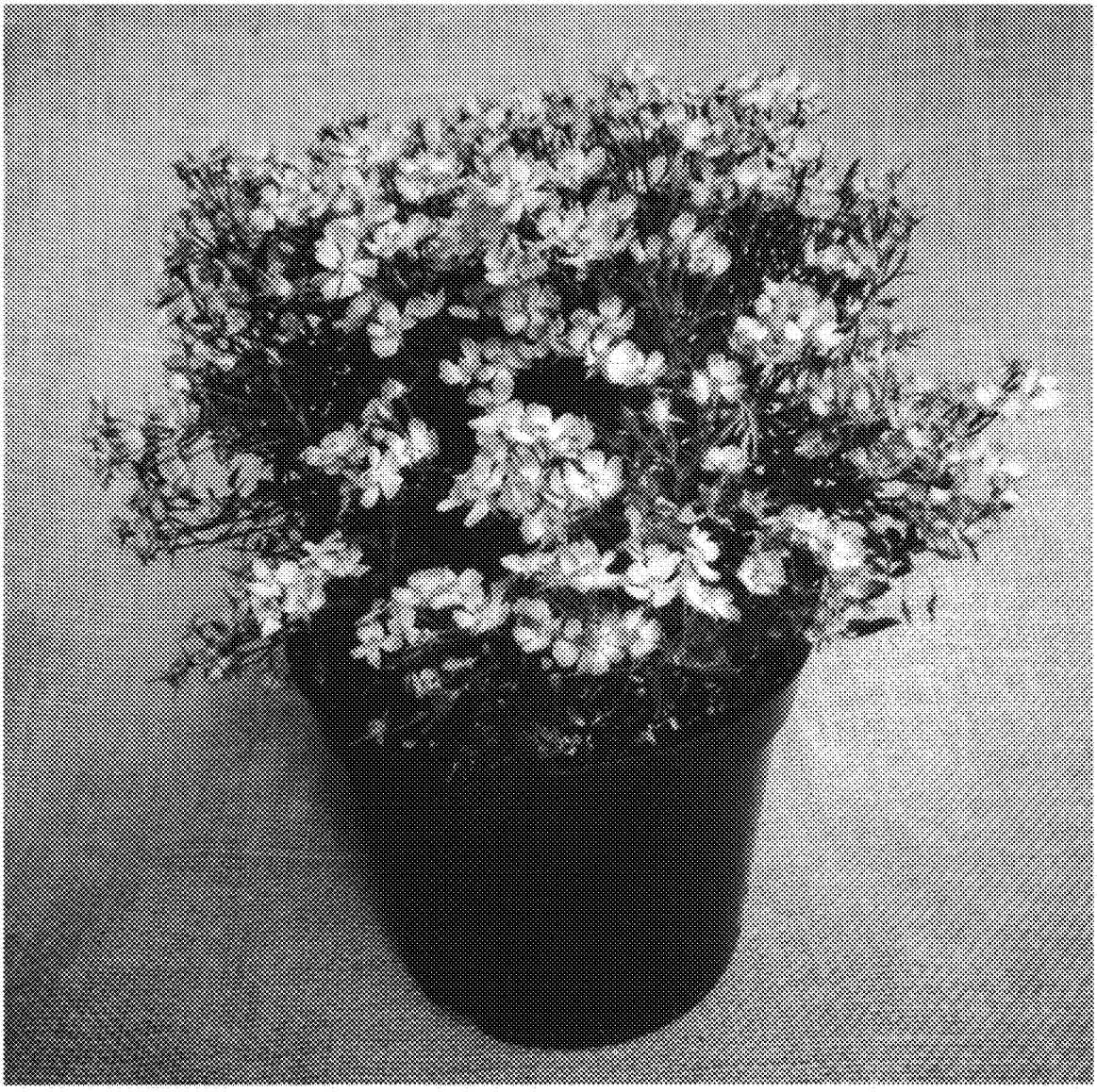
Figure 2:
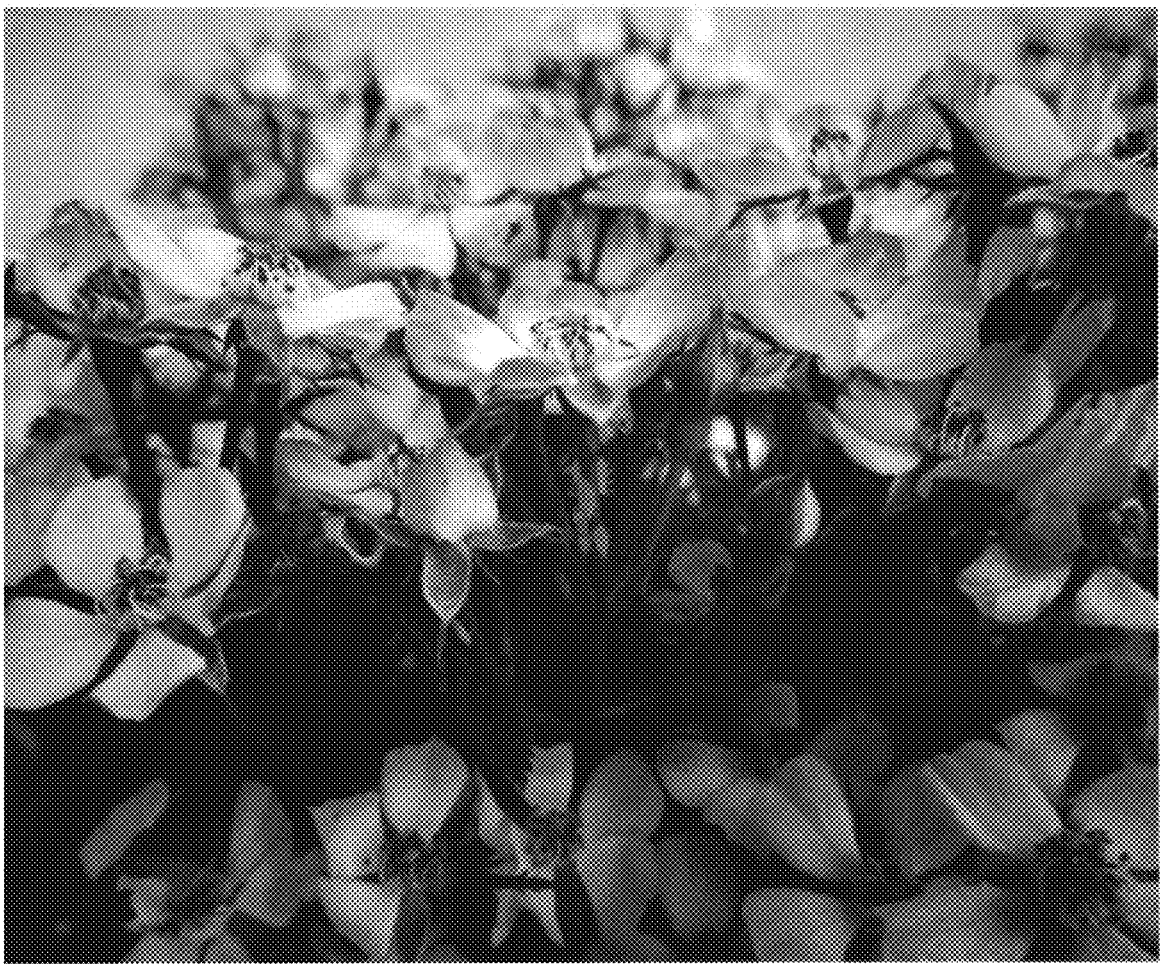

The photograph in FIG. 2 provides a close-up view of the flowers of 'ROP007'.

The colors in the photographs are as close as possible with the photographic and printing technology utilized and the color values cited in the Detailed Botanical Description accurately describe the colors of the new *Rosa*.

DETAILED BOTANICAL DESCRIPTION

The following is a detailed description of 3-year-old plants of 'ROP007' as grown in a greenhouse in a 3-liter container with a single prune in spring in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Early summer in Japan.

*Plant type*.—Herbaceous perennial.

*Plant habit*.—Mounded, upright, dwarf, groundcover.

*Height and spread*.—Reaches 10 to 15 cm in height and 25 to 30 cm in spread.

*Cold hardiness*.—At least to U.S.D.A. Zone 5.

*Diseases and pests*.—No susceptibility or resistance to diseases or pests has been observed.

*Root description*.—Fibrous, 165B in color.

*Root development*.—An average of 4 to 5 weeks for root initiation with a young rooted plant produced in 3 to 4 months from a rooted cutting.

*Propagation*.—Stem cuttings.

*Growth rate*.—Moderate.

Stem description:

*Stem shape*.—Rounded.

*Stem color*.—Young; 141C, mature; 146A.

*Stem surface*.—Smooth, covered with tiny lenticels 146D in color.

*Stem strength*.—Strong.

*Stem size*.—Up to 30 cm in length and 3 mm in diameter.

*Branching*.—An average of 10 after a single prune in spring.

*Internode length*.—4 mm to 1.5 cm.

*Thorns*.—None present.

Foliage description:

*Leaves*.—Pinnate division, alternate arrangement, held outward, lanceolate in shape, an average of 4 cm in length and 2 cm in width.

*Leaflets*.—5 per leaf (occasionally 3), ovate to elliptic in shape, cuneate base, acute apex, serrate margins, average of 1.7 cm in length and 7 mm in width, upper surface slightly rugose, glossy and glabrous, lower surface smooth, glossy and glabrous, pinnate venation pattern, color; young upper surface 143A, young lower surface 143B, mature upper surface 147A, mature lower surface 137C, upper surface veins 143C, lower surface veins 137C.

*Rachis*.—Up to 4 mm in length and 0.5 mm in diameter, upper surface glabrous and slightly canaliculate, lower surface smooth, color; upper surface 137B, lower surface 137D.

*Stipules*.—Adnate on either side of the petiole, linear in shape, glabrous surface, 1.1 cm in length, 1.5 mm in width, 147A, base 142C.

*Petioles*.—Slightly canaliculate in shape, up to 1.2 cm in length, 0.6 mm in diameter, glabrous surface, 147A, base 142C in color.

Inflorescence description:

*Inflorescence type*.—Raceme of single flowers on stem terminus.

*Inflorescence shape*.—Ovate.

*Inflorescence size*.—Up to 10 cm in height and 6 cm in diameter.

*Flower number*.—An average of 5 to 30 per raceme.

*Flower fragrance*.—Faint, pleasant scent.

*Flower longevity*.—Raceme lasts about 20 days, individual flowers 4 to 5 days.

*Flower type*.—Single, rotate.

*Flower size*.—Up to 1.8 cm in diameter and 2 mm in depth.

*Flower aspect*.—Upwards and slightly concave.

*Peduncles*.—Round in shape, up to 2 cm in length, 0.8 mm in diameter, 143B in color, glossy and glabrous surface.

*Pedicels*.—Round in shape, up to 6 cm in length and 0.6 mm in diameter, 143B in color, glossy and glabrous surface.

*Flower buds*.—Broadly ovate in shape, up to 5 mm in length, 4.5 mm in diameter, glabrous surface, N66C, base 157C.

*Sepals*.—5 (2 are smaller and 3 are larger), rotate in arrangement, lanceolate in shape, acuminate apex, truncate base, up to 1.2 cm in length and 3 mm in width, inner surface glossy and densely covered with woolly hairs, outer surface glossy and sparsely covered with woolly hairs, entire margins with an average of 3 very fine leafy appendages on each side about 2 mm in length present, color; inner surface 139A on larger sepals and 139C and smaller sepals, outer surface 139C on larger sepals and 141B on smaller sepals.

*Petals*.—5, persistent, rotate in arrangement, broadly obovate in shape, up to 7.5 mm in length, 6 mm in width, obtuse to rounded apex, entire margins, cuneate base, glabrous surfaces, color; upper surface when opening N57C, base NN155D, lower surface when opening N57A, base NN155D, upper surface when fully open N66D, base NN155D, lower surface when fully open N57A, base NN155D.

*Bracts*.—Simple, oblanceolate in shape, up to 1.1 cm in length, 2.5 mm in width, acute apex, serrate margins, base is cuneate and slightly wider up to 2.5 mm, color; upper surface 147A, base 142C, lower surface 147A, base 142B, both surfaces glossy and margins densely covered with long woolly hairs.

*Receptacle*.—Ovate in shape, 3 mm in length, 2.2 mm in diameter, glossy and moderately covered with woolly hairs, 143C in color.

Reproductive organs:

*Gynoecium*.—Pistil; 1, syncarpous, average of 10 styles with stigmas, stigma an average of 1 mm in length and 143D in color, style; up to 2.5 mm in length, 143D in color, glabrous surface, ovary; 2 mm in length, 1.5 mm in width, 144C in color, glabrous surface.

*Androecium*.—An average of 60 stamens, filaments; up to 3 mm in length and NN155D in color, anthers; kidney shaped, an average of 0.6 mm in length and 0.7 mm in width, N167B in color with margins 167D, pollen; moderate in quantity and 167D in color.

*Fruit and seed*.—None observed, fruit is not produced.

It is claimed:

1. A new and distinct cultivar of *Rosa* plant named 'ROP007' as herein illustrated and described.

* * * * *